United States Patent [19]

Itatani et al.

[11] Patent Number: 4,539,423

[45] Date of Patent: Sep. 3, 1985

[54] PROCESS FOR PREPARING DIESTERS OF MALONIC ACID

[75] Inventors: Hiroshi Itatani; Mikito Kashima; Tsutomu Suehiro, all of Ichihara, Japan

[73] Assignee: Ube Industries Ltd., Ube, Japan

[21] Appl. No.: 433,045

[22] Filed: Oct. 6, 1982

[30] Foreign Application Priority Data

Oct. 15, 1981 [JP] Japan ................................ 56-163487

[51] Int. Cl.$^3$ .............................................. C07C 67/36
[52] U.S. Cl. ...................................... 560/204; 556/30; 556/13; 556/23; 556/21; 502/162; 502/164; 502/200; 502/213
[58] Field of Search ..................... 560/204; 252/431 R, 252/431 C, 431 P; 260/429 J, 441; 502/162, 164, 200, 213

[56] References Cited

U.S. PATENT DOCUMENTS

| | | | |
|---|---|---|---|
| 4,065,490 | 12/1977 | Zehner | 560/204 |
| 4,076,949 | 2/1978 | Zehner | 560/204 |
| 4,230,881 | 10/1980 | Romano et al. | 560/193 |
| 4,256,908 | 3/1981 | Nishimura et al. | 560/204 |
| 4,281,174 | 7/1981 | Current | 560/204 |

Primary Examiner—Natalie Trousof
Assistant Examiner—Vera C. Clarke
Attorney, Agent, or Firm—Frishauf, Holtz, Goodman & Woodward

[57] ABSTRACT

Disclosed is an improved process for preparing diesters of malonic acid by subjecting ketene, carbon monoxide and an ester of nitrous acid to a liquid phase reaction in an organic solvent, in which the reaction is carried out in the presence of a catalyst of a platinum group metal complex represented by the formula:

$$L_2MX_2$$

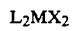

wherein, L represents a ligand selected from the group consisting of triorganophosphines, triorganophosphite and triorganoarsines; M represents a platinum group metal; and X represents a halogen or an acetic acid ion.

21 Claims, No Drawings

PROCESS FOR PREPARING DIESTERS OF MALONIC ACID

This invention relates to a process for preparing diesters of malonic acid. More particularly, it relates to a process for preparing diesters of malonic acid by employing ketene, carbon monooxide and an ester of nitrous acid as the starting materials.

Diesters of malonic acid are of value as starting materials for preparing malonic acid, barbituric acid, barbitals, as well as sources for producing pharmaceuticals and agricultural chemicals.

Heretofore, diesters of malonic acid have been prepared by reacting monochloroacetic acid with sodium cyanide in the presence of an alkali hydroxide to give sodium cyanoacetate which, in turn, is hydrolyzed and further esterified to obtain the desired diesters. The process, however, appears unsatisfactory from the economical viewpoint since the process involves complicated procedures and produces a large amount of waste water containing cyanide ions.

There have been proposed various processes for preparing diesters of malonic acid by reacting an ester of haloacetic acid, carbon monooxide and an alcohol. For instance, Japanese Laid-open Patent Application No. 111015/1975 conducts the process in the presence of a metal carbonyl catalyst and a basic compound. Japanese Laid-open Patent Application No. 146414/1976 conducts the process in the presence of a cobalt-containing compound catalyst and an alcoholate of an alkali or alkaline earth metal or an alcoholic alkali hydroxide.

Japanese Laid-open Patent Application No. 100417/1977 conducts the process in the presence of a basic compound and a rhodium catalyst and, if desired, an iodine-containing compound.

Furthermore, Japanese Laid-open Patent Application No. 7613/1978 a process of reacting methylene dihalide, carbon monooxide and an alcohol in the presence of a cobalt carbonyl catalyst.

When the above-mentioned prior art processes are applied to industrial purposes, however, they involve diverse drawbacks such as the use of expensive esters of haloacetic acid, the necessity of using a large amount of alkali for absorbing the halogen evolved during the reaction and use of such disadvantageous catalysts as a cobalt carbonyl, which is difficult to be recycled efficiently, or an expensive rhodium or iodine compound.

In view of the above-mentioned situation, there have been made various studies for the purpose of obtaining a process for preparing diesters of malonic acid that is superior from the industrial aspect. As the result, it has been found that diesters of malonic acid may be produced, by simple operations, by contacting ketene, carbon monooxide and an ester of nitrous acid in an organic solvent, i.e. in the state of liquid phase, in the presence of a palladium metal or a salt thereof, as disclosed in U.S. Pat. No. 4,256,908.

This invention relates to an improved process of the above-mentioned method and provides a process for preparing diesters of malonic acid which is characterized by subjecting ketene, carbon monooxide and an ester of nitrous acid to a liquid phase homogeneous reaction in an organic solvent in the presence of a platinum group metal complex represented by the general formula (I):

$$L_2MX_2 \quad (I)$$

(wherein, L represents a ligand selected from the group consisting of triorganophosphines, triorganophosphites and triorganoarsines, M represents a platinum group metal, and X represents a halogen or an acetic acid ion).

This invention for preparing diesters of malonic acid is identical with the above-mentioned invention disclosed in the U.S. Pat. No. 4,256,908, in that the reaction is performed by reacting ketene, carbon monooxide and an ester of nitrous acid in a liquid phase, following the reaction formula (A):

$$CH_2CO + CO + 2RONO \rightarrow CH_2(COOR)_2 + 2NO \quad (A).$$

This invention, however, is different in that a complex having a specific composition is employed as the catalyst and that the reaction is performed in a homogeneous system.

Namely, in the above prior art process for preparing diesters of malonic acid using a palladium metal or a salt thereof, the reaction proceeds in a heterogeneous system by suspending the catalyst in a solvent, which tends to produce various by-products and involves drawbacks such as difficulty in separation and purification of the desired diester of malonic acid, abrasion or choking of the reaction vessel caused by the catalyst present in the reaction mixture in the suspension state, and complicated procedures for recovery and reuse of the catalyst; these drawbacks are desired to be eliminated for the practical application.

This invention is to solve the above-mentioned problems by adopting a complex catalyst having a specific composition and by performing the liquid phase reaction in a homogeneous system. Namely, this invention attains not only higher yield of the desired product and improved selectivity based on ketene, but also greatly extended catalyst activity, when compared with any of the conventional processes for preparing diesters of malonic acid or with the improved process disclosed in the U.S. Pat. No. 4,256,908.

Thus, the present process is quite advantageous as a practically industrial process for the production of diesters of malonic acid.

The invention is further explained more in detail as follows.

The starting materials for the process according to this invention are ketene, carbon monooxide and an ester of nitrous acid. The ester of nitrous acid to be employed in the process according to the invention is an ester of a saturated monovalent aliphatic alcohol or an alicyclic alcohol having from 1 to 8 carbon atoms with nitrous acid. As the alcohol constituent, there may be mentioned, for example, aliphatic alcohols such as methanol, ethanol, n-(and iso-)propanol, n-(and iso-, sec-, tert-)butanol, n-(and iso-)amyl alcohol, hexanol or octanol, and alicyclic alcohols such as cyclohexanol or methylcyclohexanol. The alcohol may have substituent(s) that does not interfere with the reaction, such as an alkoxy group.

The ester of nitrous acid is not necessarily in the form of ester itself. Alternatively, starting materials that form an ester of nitrous acid in situ in the reaction system may be employed. Namely, it is also advantageous to employ, in place of ester of nitrous acid, an alcohol and a nitrogen oxide selected from the group consisting of nitrogen monooxide, nitrogen dioxide, dinitrogen trioxide and dinitrogen tetraoxide, or a hydrate thereof, accompanied if necessary, by introduction of a gas containing molecular oxygen. The hydrate of nitrogen oxide is preferably exemplified by nitric acid and nitrous acid. Where an alcohol is employed, any alcohol mentioned for the alcohol constituent of the ester of nitrous acid may appropriately be chosen.

The catalyst to be employed in the present invention is a platinum group metal complex having the general formula (I):

$$L_2MX_2 \qquad (I)$$

In the above general formula (I), L represents a ligand selected from the group consisting of triorganophosphines, triorganophosphites and triorganoarsines. Examples of triorganophosphines include trialkylphosphines containing alkyl groups having from 1 to 8 carbon atoms, such as trimethylphosphine, triethylphosphine, tri-n-(or iso)propylphosphine or tri-n-(or iso-, tert-)butylphosphine; triarylphosphines containing aryl groups having from 6 to 12 carbon atoms, such as triphenylphosphine, tri-substituted phenylphosphine, tritolylphosphine, tri-p-chlorophenylphosphine or trimethoxyphenylphosphine; and 1,2-bisdiphenylphosphinoethane. Examples of triorganophosphites include trialkylphosphites containing alkyl groups having from 1 to 8 carbon atoms, such as trimethylphosphite, triethylphosphite, tri-n-(or iso)propylphosphite, or tri-n-(or iso-, tert-)butylphosphite; and triarylphosphites containing aryl groups having from 6 to 12 carbon atoms, such as triphenylphosphite, tr-substituted phenylphosphite, tritolylphosphite, tri-p-chlorophenylphosphite or trimethoxyphenylphosphite. Examples of triorganoarsines include trialkylarsines containing alkyl groups having from 1 to 8 carbon atoms, such as trimethylarsine, triethylarsine, tri-n-(or iso-)propylarsine or tri-n-(or iso-, tert-)butylarsine; triarylarsines containing aryl groups having from 6 to 12 carbon atoms, such as triphenylarsine, tri-substituted phenylarsine, tritolylarsine, tri-p-chlorophenylarsine or trimethoxyphenylarsine; and 1,2-bis-diphenylarsinoethane.

In the general formula (I), M represents a platinum group element such as platinum or palladium, and X represents chlorine, bromine or iodine or acetic acid ion ($CH_3COO^-$).

This complex catalyst of the general formula (I) may be prepared, for example, according to the following reaction scheme (B):

$$MX_2 + 2L \rightarrow L_2MX_2 \qquad (B)$$

In the above reaction scheme, M, X and L have the meaning defined above.

One of the specific examples of the above scheme is a reaction of palladium chloride ($PdCl_2$) with triphenylphosphine [$(C_6H_5)_3P$] to give bistriphenylphosphinedichloropalladium i.e. [$(C_6H_5)_3P]_2PdCl_2$ in an aqueous ethyl alcohol.

The reaction represented by the scheme (B) proceeds very rapidly to give a complex instantaneously. Hence, the complex may not necessarily be introduced into the reaction system of the invention in the form of the complex.

Namely, stoichiometric amounts of respective components represented by the reaction scheme (B) may be added separately to the reaction system, whereby the complex is formed in situ in the reaction system to play the role of catalyst.

The platinum group metal complex catalyst is preferably present in the reaction system according to the process of the invention within the range of from 0.1 to 100 mmoles, preferably 1 to 20 mmoles from an economical viewpoint, per liter of the reaction solvent.

In performing the process according to the invention, it is preferable that there are present in the reaction system, besides the platinum group metal complex catalyst, a nitrogen-containing compound such as amide, a tertiary amine or a quaternary ammonium salt and/or a halide of a metal belonging to IVb of the periodic table such as germanium or tin.

The nitrogen-containing compound such as amides tertiary amines and quaternary ammonium salts is exemplified, for instance, by formamide, acetamide; triethylamine, diisopropylethylamine, tributylamine, diethylphenylamine; tetra-n-methylammonium chloride, tetra-n-ethylammonium chloride, tetra-n-butylammonium chloride, tetra-n-phenylammonium chloride, tetra-n-tolylammonium chloride, tetra-n-benzylammonium chloride, or their respectively corresponding bromides or iodides. This compound is preferably present in the reaction system at from 0.5 to 10, preferably 1 to 5, times the mole amount of the platinum group metal complex catalyst. The addition of this nitrogen-containing compound to the reaction system improves remarkably yield and selectivity of diesters of malonic acid that is the aimed product of the process.

The halide of a metal belonging to IVb of the periodic table such as germanium or tin may be exemplified, for instance, by stannous chloride, stannous bromide, stannous iodide, germanous chloride, germanous bromide or germanous iodide. The halide is preferably present in the reaction system at from 0.5 to 10, preferably 1 to 5, times the mole amount of the platinum group metal complex catalyst. The addition of the halide to the reaction system improves remarkably stability of the complex catalyst, whereby the phenomenon that the catalyst precipitates as insolubles during the reaction will not take place at all.

The above-mentioned nitrogen-containing compound and the halide may be present in the reaction system solely or in combination.

As described above, the process of the invention is based on the liquid phase homogeneous reaction. Accordingly, the platinum group metal complex catalyst of the invention must be dissolved in an organic solvent in the reaction system. In order to attain this, the organic solvent to be employed in the invention should be chosen from organic solvents that dissolve the platinum group metal complex catalyst of the general formula (I).

The organic solvent is exemplified, for instance, by halogenated aliphatic hydrocarbons such as chloroform, trichloroethane or tetrachloroethane, aromatic and halogenated aromatic hydrocarbons such as toluene, xylene, decalin, tetralin, chlorobenzene or dichlorobenzene; esters such as oxalic acetic or carbonic acid esters; ethers such as dioxane or diethlene glycol dimethyl ether; dimethylaniline; and N-methylpyrrolidone (NMP).

During the reaction, a solution of the triorganophosphine, triorganophosphite or triorganoarsine and the halide of IVb group metal in the organic solvent (e.g. a solution of triphenylphosphine and stannous chloride in N-methylpyrrolidone) may be supplied periodically to the above-mentioned reaction system, whereby the activity of the complex catalyst is maintained for a longer period of time and higher yield of the aimed product is attained.

Further, a solvent system comprising a mixture of N-methylpyrrolidone and aliphatic hydrocarbon may be employed in the reaction system, whereby the life of the complex catalyst may be prolonged advantageously, and also, it becomes easier to separate catalyst layer from product layer.

In performing the process of the invention, the platinum metal group complex catalyst of the general formula (I) and, if necessary, the nitrogen-containing compound and/or the halide of a metal belonging to IVb of the periodic table are dissolved in an organic solvent, then ketene, carbon monoxide and an ester of nitrous acid are added thereto to effect the reaction.

The feeding rate of ketene to the reaction liquid is preferably maintained within the range of from 1 to 200 ml/l (0.045 to 8.9 mmole/min) (reaction liquid) per minute. Meanwhile, the ester of nitrous acid is preferably fed into the reaction liquid at the rate of not less than 2 times moles based on ketene. The reaction is preferably performed at temperature of from ambient to 200° C. and under the partial carbon monooxide pressure of not less than 0.5 kg/cm$^2$.G.

The diester of malonic acid, which is the aimed product of the invention, may be obtained by subjecting the reaction mixture to solvent extraction and then to distillation. The thus obtained diester of malonic ester is a diester containing carboxyl groups corresponding to the alcohol constituents of the ester of nitrous acid as the starting material.

The residue, from which organic solvent, unreacted starting materials and diester of malonic acid have been separated out, contains a large portion of the platinum group metal complex catalyst intact, hence, the residue containing the catalyst may be used as such, or after reactivating the catalyst, for the subsequent reactions. Accordingly, in the process of the invention, any specific procedures for the recovery of catalyst, or apparatus or operation for the reuse thereof are not required. This is also a significant advantage of the present process from the practical, industrial aspect.

The present invention will be explained by the following working examples.

EXAMPLE 1

Into a 300 ml four-necked flask were charged bistriphenylphosphinedichloropalladium (0.702 g, 1 mmole), triethylamine (0.101 g, 1 mmole), stannous chloride (0.190 g, 1 mmole) and n-amyl nitrite (10 ml, 73 mmoles), together with tetrachloroethane (200 ml). The reaction mixture was heated at 80° C. with stirring, then nitrogen gas containing 1.8 volume percent (0.096 mmole/min) of ketene, and carbon monooxide were introduced to the reaction mixture at the rate of 120 ml/min and 100 ml/min, respectively. A further n-amyl nitrite was added every 3 hours (10 ml, 73 mmoles, each time), and the reaction was performed for 12 hours. Thereafter, the reaction mixture was cooled to room temperature, the solvent was distilled off and the reaction product in the residue was analyzed by gas chromatography. The results will be shown in Table 1, which contains also results obtained in the subsequent working examples.

EXAMPLE 2

Following the procedures of Example 1, the reaction was performed for 6 hours, except that no stannous chloride was added and that ketene content in nitrogen gas was maintained at 2.1 volume percent (0.11 mmole/min). The reaction product was subjected to analysis.

EXAMPLE 3

By using the same reaction vessel as in Example 1, palladium chloride (0.177 g, 1 mmole), triphenylphosphine (0.524 g, 2 mmoles) and triethylamine (0.101 g, 1 mmole) were dissolved in tetrachloroethane (200 ml), then the reaction was performed following the procedures of Example 1 for 6 hours, except that ketene content in nitrogen gas was maintained at 2.0 volume percent (0.11 mmole/min). The reaction product was subjected to analysis.

EXAMPLE 4

Into the same reaction vessel as in Example 1 were charged bistriphenylphosphinediacetatepalladium (0.748 g, 1 mmole) and formamide (0.135 g, 3 mmoles), together with 1,4-dioxane (200 ml), and the mixture was heated at 80° C. with stirring. Then, nitrogen gas containing 5.0 volume percent (0.26 mmole/min) of ketene, and carbon monooxide were introduced to the reaction mixture at the rate of 120 ml/min and 100 ml/min, respectively and, at the same time, n-amyl nitrite was added dropwise to effect the reaction for 2 hours. The total amount of n-amyl nitrite added was 25 ml (182.5 mmoles). The reaction product was subjected to analysis by the same method as in Example 1.

EXAMPLE 5

Into the same reaction vessel as in Example 1 were charged palladium acetate (0.244 g, 1 mmole), triphenylphosphine (0.524 g, 2 mmoles), triethylamine (0.101 g, 1 mmole) and n-amyl nitrite (10 ml, 73 mmoles), together with trichloroethane (200 ml). The mixture was heated at 80° C. with stirring, then nitrogen gas containing 2.3 volume percent (0.12 mmole/min) of ketene, and carbon monooxide were introduced to the mixture at the rate of 120 ml/min and 100 ml/min, respectively.

After 3 hours, a further n-amyl nitrite (10 ml, 73 mmoles) was added and the reaction was performed for 6 hours. The reaction product was subjected to analysis.

EXAMPLE 6

Into the same reaction vessel as in Example 1 were charged bistriphenylarsinedichloropalladium (0.790 g, 1 mmole), stannous chloride (0.190 g, 1 mmole), triethylamine (0.101 g, 1 mmole) and n-amyl nitrite (10 ml, 73 mmoles), together with tetrachloroethane (200 ml). The mixture was heated at 80° C. with stirring, then nitrogen gas containing 2.1 volume percent (0.11 mmole/min) of ketene, and carbon monooxide were introduced at the rate of 120 ml/min and 100 ml/min, respectively, to perform the reaction for 3 hours. The reaction product was subjected to analysis.

EXAMPLE 7

The procedures of Example 6 were followed to perform the reaction for 3 hours, except that the catalyst system containing palladium chloride (0.177 g, 1 mmole), tri-n-butylphosphine (0.404 g, 2 mmoles) and triethylamine (0.101 g, 1 mmole) was employed and no stannous chloride was added. The reaction product was subjected to analysis.

EXAMPLE 8

Into the same reaction vessel as in Example 1 were charged bistriphenylphosphitedichloropalladium (0.773 g, 1 mmole), triethylamine (0.101 g, 1 mmole), stannous chloride (0.190 g, 1 mmole) and n-amyl nitrite (10 ml, 73 mmoles), together with tetrachloroethane (200 ml), then the reaction was performed under the same conditions as in Example 3 for 3 hours. The reaction product was subjected to analysis.

The results obtained by respective Examples are indicated in Table 1.

TABLE 1

| Example | Amount of starting compound (mmole) ketene | ester of nitrous acid | Diester of malonic acid amount produced (mmole) | selectivity (%) | yield (%) |
|---|---|---|---|---|---|
| 1 | 71.4 | 292 | 68.5 | 95.6 | 95.9 |
| 2 | 37.1 | 146 | 31.3 | 98.7 | 84.3 |
| 3 | 34.6 | 146 | 32.3 | 95.6 | 93.3 |
| 4 | 29.0 | 182 | 12.1 | 84.7 | 41.7 |
| 5 | 40.4 | 146 | 22.4 | 96.8 | 55.4 |
| 6 | 18.0 | 73 | 14.1 | 90.3 | 78.3 |
| 7 | 18.7 | 73 | 9.6 | 92.3 | 51.3 |
| 8 | 17.7 | 73 | 4.1 | 76.2 | 23.2 |

Remarks:
The selectivity was based on the content of the diester of malonic acid relative to malonate, carbonate, oxalate and succinate of the reaction product and the yield was based on the feeding amount of ketene.

EXAMPLE 9

Into a 300 ml 4-necked flask were charged bistriphenylphosphinedibromopalladium (0.0791 g, 1 mmole), anhydrous stannous chloride (0.380 g, 2 mmoles) and tetra-n-butylammonium chloride (0.555 g, 2 mmoles), together with monochlorobenzene (200 ml) and n-amyl nitrite (50 ml, 341.5 mmoles). The flask was placed in an oil bath kept at a temperature of 90° C., then ketene, carbon monooxide and nitrogen were introduced to the liquid at the rate of 16.8 ml/min (0.75 mmole/min), 300 ml/min and 100 ml/min, respectively, and the reaction was effected for 3 hours. Upon completion of the reaction, the solvent was distilled off and the reaction product was analyzed quantitatively by gas chromatography at 200° C., using a column containing apiezone grease. It turned out that di-n-amyl malonate (105.9 mmoles, 78.3% yield based on the ketene) and n-amyl acetate (12.1 mmoles, 9.0% yield based on the ketene) were produced, respectively.

EXAMPLE 10

The procedures of Example 9 were followed, except that 85 ml (569.6 mmole) of n-amyl nitrite and 31.6 ml/min (1.41 mmole/min) of ketene were employed. The reaction product was analyzed to determine the contents of di-n-amyl malonate (219.7 mmoles, 86.5%) and n-amyl acetate (34.3 mmoles, 13.5%).

EXAMPLE 11

To the same reaction vessel as in Example 9 were charged bistriphenylphosphinedibromopalladium (0.396 g, 0.5 mmole), stannous chloride (0.190 g, 1 mmole), tetra-n-butylammonium chloride (0.278 g, 1 mmole) and n-amyl nitrite (25 ml, 171.0 mmoles), together with monochlorobenzene (200 ml). Then, ketene, carbon monooxide and nitrogen were introduced to the mixture at the rate of 26.4 ml/min (1.18 mmole/min), 300 ml/min and 100 ml/min, respectively, and the reaction was performed at 90° C. for 3 hours. During the reaction, a further n-amyl nitrite (50 ml, 342.0 mmoles) was added dropwise to the reaction mixture over 2.5 hours. The reaction mixture was analyzed by gas chromatography, revealing that di-n-amyl malonate (125.6 mmoles, 59.1%) and n-amyl acetate (24.7 mmoles) were obtained.

EXAMPLE 12

The procedures of Example 11 were followed, except that ketene was introduced at the rate of 32.0 ml/min (1.43 mmole/min) and that triphenylphosphine (0.066 g, 0.25 mmole) was dissolved in the further added n-amyl nitrite (50 ml). The reaction proceeded smoothly for three hours, during which no deactivation of the catalyst was observed. The reaction product was analyzed by gas chromatography, revealing that n-di-amyl malonate (165.6 mmoles, 64.5%) and n-amyl acetate (32.9 mmoles, 12.8%) were obtained.

EXAMPLE 13

To the same reaction vessel as in Example 9 were charged bistriphenylphosphinedibromopalladium (0.198 g, 0.25 mmole), stannous chloride (0.095 g, 0.5 mmole), tetra-n-butylammonium chloride (0.139 g, 0.5 mmole) and n-amyl nitrite (60 ml, 406.6 mmoles), together with monochlorobenzene (200 ml). Then, ketene, carbon monooxide and nitrogen were introduced to the mixture at the rate of 10.4 ml/min (0.46 mmole/min), 300 ml/min and 100 ml/min, respectively, and the reaction was effected for 5 hours. During the reaction, 10 ml of a solution of triphenylphosphine and stannous chloride (0.25 mmole each) in N-methylpyrrolidone was added to the reaction system in 2.5 ml portions every 1 hour. The reaction proceeded smoothly for 5 hours without termination of the reaction to give di-n-amyl malonate (116.2 mmoles, 83.8%) and n-amyl acetate (20.5 mmoles, 14.7%).

EXAMPLE 14

To the same reaction vessel as in Example 9 were charged bistriphenylphosphinedibromopalladium (0.198 g, 0.25 mmole), stannous chloride (0.095 g, 0.5 mmole), tetra-n-butylammonium chloride (0.139 g, 0.5 mmole) and n-amyl nitrite (70 ml, 474.4 mmoles), together with n-heptane (150 ml) and N-methylpyrrolidone (50 ml). Then, ketene, carbon monooxide and nitrogen were introduced to the mixture at the rate of 10.1 ml/min (0.45 mmole/min), 300 ml/min and 100 ml/min, respectively, and the reaction was effected at 90° C. for 5 hours. The reaction product was analyzed by gas chromatography, revealing that di-n-amyl malonate (82.3 mmoles, 60.7%) and n-amyl acetate (25.5 mmoles, 18.8%) were obtained.

EXAMPLE 15

The procedures of Example 14 were followed, except that 80 ml (536.9 mmoles) of n-amyl nitrite was used and that ketene was introduced at the rate of 11.3 ml/min (0.50 mmole/min). During the reaction, however, 15 ml, of a solution of triphenylphosphine (0.092 g, 0.375 mmole) and stannous chloride (0.072 g, 0.375 mmole) in N-methylpyrrolidone was added to the reaction system in 2.5 ml portions every 1 hour, and the reaction was effected at 90° C. for 6 hours. The gas chromatographic analysis revealed that di-n-amyl malonate (136.0 mmoles, 74.8%) and n-amyl acetate (45.4 mmoles, 25.0%) were obtained.

EXAMPLE 16

To the same reaction vessel as in Example 9 were charged bistriphenylphosphinedibromopalladium (0.198 g, 0.25 mmole), stannous chloride (0.095 g, 0.5 mmole), tetra-n-butylammonium chloride (0.139 g, 0.5 mmole) and n-amyl nitrite (55 ml, 368.9 mmoles), together with n-heptane (175 ml) and N-methylpyrrolidone (25 ml). Then, ketene, carbon monooxide and nitrogen were introduced to the mixture at the rate of 11.4 ml/min (0.51 mmole/min), 300 ml/min and 100 ml/min, respectively, and the reaction was effected at 90° C. for 4 hours. During the reaction, 10 ml of a solution of triphenylphosphine (0.061 g, 0.25 mmole) and stannous chloride (0.0475 g, 0.25 mmole) of N-methylpyrrolidone was added to the reaction system in 2.5 ml portions every 1 hour. The gas chromatographic analysis revealed that di-n-amyl malonate (103.9 mmoles, 84.9%) and n-amyl acetate (17.1 mmoles, 14.0%) were obtained.

EXAMPLE 17

To the reaction product obtained in Example 16 were added n-hexane (500 ml) and N-methylpyrrolidone (25 ml), causing the mixture to be separated into two layers. Then, 20 ml of the lower layer containing the catalyst was taken out, further triphenylphosphine (0.25 mmole) and stannous chloride (0.25 mmole) were added, and the mixture was reacted under the same conditions as in Example 16. The gas chromatographic analysis revealed that di-n-amyl malonate (95.3 mmoles, 77.8%) and n-amyl acetate (20.5 mmoles, 16.7%) were obtained.

EXAMPLE 18

The procedures of Example 10 were followed, except that the n-amyl nitrite was replaced by 45 ml (570.0 mmoles) of ethyl nitrite. As a result, obtained were ethyl malonate (203.5 mmoles, 80.1%) and ethyl acetate (24.1 mmoles, 9.5%).

EXAMPLE 19

The procedures of Example 10 were followed, except that tri-n-butylphosphinedibromopalladium (0.671 g, 1 mmole) was employed as the complex catalyst. As a result, obtained were di-n-amyl malonate (170.5 mmoles, 67.1%) and n-amyl acetate (35.6 mmoles, 14.0%).

EXAMPLE 20

To the same reaction vessel as in Example 9 were charged bistriphenylphosphinedibromopalladium (0.791 g, 1 mmole), stannous bromide (0.558 g, 2 mmoles) and tetra-n-ethylammonium bromide (0.420 g, 2 mmoles), together with n-amyl nitrite (50 ml, 356.0 mmoles) and chlorobenzene (200 ml). Then, nitrogen gas containing 10.0 vol.% of ketene and carbon monooxide were introduced to the mixture at the rate of 116.1 ml/min and 200 ml/min, respectively, and the reaction was performed at 90° C. for 3 hours. The reaction mixture was analyzed to reveal that di-n-amyl malonate (63.0 mmoles, 49.4%) and n-amyl acetate (36.5 mmoles, 28.3%) were obtained.

EXAMPLE 21

To the same reaction vessel as in Example 9 were charged bistriphenylphosphinedichloropalladium (0.702 g, 1 mmole), stannous chloride (0.190 g, 1 mmole) and tetra-n-ethylammonium chloride (0.166 g, 1 mmole) together with n-amyl nitrite (50 ml, 350.5 mmoles) and chlorobenzene (200 ml). The reaction mixture was maintained at 100° C. with stirring, and introduced thereto were nitrogen gas containing 16.4 vol.% of ketene and carbon monooxide at the rate of 119.6 ml/min and 200 ml/min, respectively. The reaction was performed for 3 hours. The reaction mixture was analyzed to reveal that di-n-amyl malonate (115.3 mmoles, 73.2%) and n-amyl acetate (24.1 mmoles, 15.3%).

We claim:

1. A process for preparing diesters of malonic acid which comprises subjecting ketene, carbon monoxide and an ester of nitrous acid to a liquid phase homogeneous reaction in an organic solvent in the presence of a catalyst of a platinum group metal complex represented by the formula:

$$L_2MX_2$$

wherein, L represents a ligand selected from the group consisting of a triorganophosphines, triorganophosphites and triorganoarsines; M represents a platinum group metal; and X represents a halogen or an acetic acid ion.

2. The process of claim 1, wherein said ligand represented by L is selected from the group consisting of trialkylphosphines, triarylphosphines, trialkylphosphites, triarylphosphites, trialkylarsines and triarylarsines; said platinum group metal represented by M is a platinum ion or a palladium ion; and said halogen represented by X is a chlorine, bromine or iodine.

3. The process of claim 2, wherein said L is a triphenylphosphine, M is a palladium ion and X is bromine.

4. The process of claim 3, wherein said X is chlorine.

5. The process of claim 1, wherein said platinum group metal complex catalyst is present in an amount of from 0.1 to 100 mmoles per liter of the solvent.

6. The process of claim 5, wherein said catalyst is present in an amount of from 1 to 20 mmoles per liter of the solvent.

7. The process of claim 1, further comprising conducting said reaction with at least one compound selected from the group consisting of nitrogen containing compounds selected from the group consisting of amides, tertiary amines, and quaternary ammonium salts, and a halide of germanium or tin.

8. The process of claim 7, wherein said nitrogen-containing compound is triethylamine or tetra-n-butylammonium chloride, and said halide is stannous chloride.

9. The process of claim 7, wherein said nitrogen-containing compound and said halide are each present in an amount of from 0.5 to 10 times the mole amount of the platinum group metal complex catalyst.

10. The process of claim 1, wherein said organic solvent is selected from the group consisting of halogenated aliphatic hydrocarbons, aromatic hydrocarbons, halogenated aromatic hydrocarbons, esters, ethers, diethylaniline and N-methylpyrrolidone.

11. The process of claim 1, wherein said organic solvent is a mixture of N-methylpyrrolidone and an aliphatic hydrocarbon.

12. The process of claim 9 wherein said nitrogen-containing compound and said halide are each present in an amount of from 1–5 times the mole amount of the platinum group metal complex catalyst.

13. The process of claim 1, wherein said ester of nitrous acid is formed in situ during said reaction.

14. The process of claim 7, wherein said ester of nitrous acid is formed in situ during said reaction.

15. A process for preparing diesters of malonic acid which comprises subjecting ketene, carbon monoxide and an ester of nitrous acid to a liquid phase homogeneous reaction in an organic solvent selected from the group consisting of halogenated aliphatic hydrocarbons, aromatic hydrocarbons, halogenated aromatic hydrocarbons, esters, ethers, diethylaniline and N-methylpyrrolidone in the presence of a catalyst of a platinum group metal complex represented by the formula:

$$L_2MX_2$$

wherein L is a ligand selected from the group consisting of trialkylphosphines, triarylphosphines, trialkylphosphites, triarylphosphites, trialkylarsines and triarylarsines; M is a platinum ion or a palladium ion; and X is a halogen ion or an acetic acid ion, said platinum group metal complex being present in an amount of from 0.1 to 100 mmoles per liter of the solvent.

16. The process of claim 15, wherein said catalyst is present in an amount of from 1 to 20 mmoles per liter of the solvent.

17. The process of claim 15, further comprising conducting said reaction with at least one compound selected from the group consisting of nitrogen-containing compounds selected from the group consisting of amides, tertiary amines, and quaternary ammonium salts, and a halide of germanium or tin.

18. The process of claim 17, wherein said nitrogen-containing compound is triethylamine or tetra-n-butylammonium chloride, and said halide is stannous chloride.

19. The process of claim 17, wherein said nitrogen-containing compound and said halide are each present in an amount of from 0.5 to 10 times the mole amount of the platinum group metal complex catalyst.

20. The process of claim 15, wherein said organic solvent is a mixture of N-methylpyrrolidone and an aliphatic hydrocarbon.

21. The process of claim 15, wherein said ester of nitrous acid is formed in situ during said reaction.

* * * * *